United States Patent
Spickermann

(10) Patent No.: US 6,379,617 B1
(45) Date of Patent: *Apr. 30, 2002

(54) DIALYSIS MACHINE AND PROCESS FOR ITS DISINFECTION

(75) Inventor: Reiner Spickermann, Wasserlosen-Burghausen (DE)

(73) Assignee: Fresenius Medical Care Deutschland GmbH, Bad Homburg (DE)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 08/942,931

(22) Filed: Oct. 2, 1997

(30) Foreign Application Priority Data

Oct. 2, 1996 (DE) .......................... 196 40 840

(51) Int. Cl.[7] .................. A61M 1/14; A61L 9/00; B01D 11/00; C02F 1/76
(52) U.S. Cl. .................. 422/44; 422/28; 422/292; 604/5.01; 210/646; 210/753; 210/760
(58) Field of Search .................. 210/645–46, 749, 210/753–4, 756, 758–60; 422/44–48, 28–31, 1, 37, 291–2; 604/4–5, 4.01, 5.01

(56) References Cited

U.S. PATENT DOCUMENTS

| 3,819,329 | A | * | 6/1974 | Kaestner et al. ............... 21/58 |
|---|---|---|---|---|
| 4,035,981 | A | | 7/1977 | Braun et al. |
| 4,141,830 | A | * | 2/1979 | Last .......................... 210/63 |
| 4,230,571 | A | * | 10/1980 | Dadd ......................... 210/760 |
| 4,963,341 | A | | 10/1990 | Huxtable et al. |
| 5,015,541 | A | | 5/1991 | Evans |
| 5,139,675 | A | | 8/1992 | Arnold et al. |
| 5,275,784 | A | | 1/1994 | Perlaky |
| 5,292,488 | A | | 3/1994 | Cerola et al. |
| 5,306,352 | A | | 4/1994 | Nicolson et al. |
| 5,316,740 | A | * | 5/1994 | Baker et al. ................. 422/186 |
| 5,336,165 | A | * | 8/1994 | Twardowski .................... 604/5 |
| 5,407,550 | A | | 4/1995 | Shimamune et al. |
| 5,484,397 | A | | 1/1996 | Twardowski |
| 5,585,003 | A | * | 12/1996 | Van Newenhizen .......... 210/646 |
| 5,593,598 | A | * | 1/1997 | McGinness et al. ......... 210/748 |
| 5,603,897 | A | | 2/1997 | Heiler et al. |
| 5,641,456 | A | * | 6/1997 | Rosenauer .................... 422/29 |
| 5,776,351 | A | * | 7/1998 | McGinness et al. ......... 210/748 |
| 5,810,758 | A | * | 9/1998 | Yamazaki et al. .............. 604/4 |
| 6,051,188 | A | * | 4/2000 | Spickermann |
| 6,113,793 | A | * | 9/2000 | Jönsson et al. ............. 210/636 |

FOREIGN PATENT DOCUMENTS

| DE | 24 28 256 | 1/1976 |
|---|---|---|
| DE | 31 15665 | 4/1981 |
| EP | 0 722 740 | 7/1996 |
| GB | 2 094 992 | 9/1982 |
| WO | WO 93/09821 | 5/1993 |

* cited by examiner

*Primary Examiner*—Angela D. Sykes
*Assistant Examiner*—Patricia Bianco
(74) *Attorney, Agent, or Firm*—Kenyon & Kenyon

(57) ABSTRACT

Dialysis machine with means for the on-line generation of at least one disinfecting agent that can be used for the disinfection of the dialysis machine as well as the process for the disinfection of a dialysis machine.

30 Claims, 1 Drawing Sheet

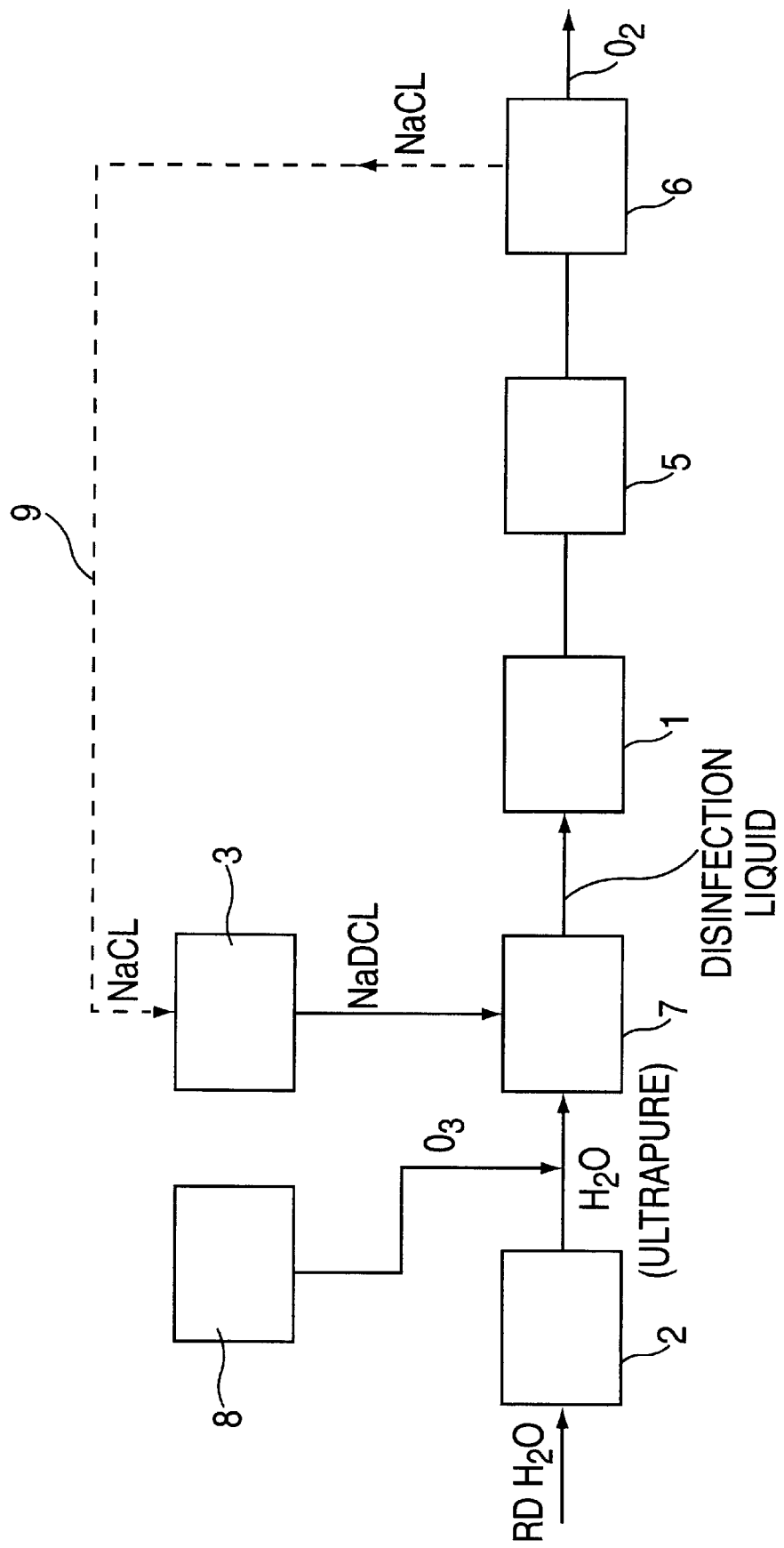

DIALYSIS MACHINE AND PROCESS FOR ITS DISINFECTION

FIELD OF THE INVENTION

The invention relates to a dialysis machine and a process for its disinfection.

BACKGROUND OF THE INVENTION

Dialysis machines must be disinfected and/or made as sterile as possible before each use.

German Patent 31 15 665 describes a hemodialysis device with a dialysis container for the storage and reception of dialysis liquid. The disclosed device is operated in such a way that, within the framework of the dialysis treatment, the dialysis liquid is not discarded after passing through the membrane unit of the dialyzer, but led back to the dialysis container. The problem of possible multiplication of microorganisms in the solution is effectively confronted by providing a UV radiation source which sterilizes the dialysis liquid before and, when necessary, for some time after the start of the treatment. In order to achieve as uniform as possible an effect of the UV treatment, the UV radiation source is introduced into a pipe located in the container that is arranged concentrically in the dialysis container or in an influx pipe for the used dialysis liquid located centrally in the container. Provided for this are materials with sufficient UV permeability between the UV radiation source and the liquid to be sterilized. The radiation at the start of and possibly for some time after the treatment has begun has the effect of being able to keep the dialysis liquid essentially sterile for the entire duration of the treatment. A further possibility of sterilizing the liquid located in the dialysis container consists of preferably arranging an infrared heat radiation attachment underneath the dialysis container by means of which the liquid located in the dialysis container can be heated for the purpose of sterilization. With a suitable design of the container, a temperature of 110° C., favorable for the purpose of sterilization, can be reached. A disadvantage of such a sterilization system is that essentially only the liquid located in the dialysis container is sterilized, whereas direct cleaning of the pipes and other structural components distant from it is not possible.

In U.S. Pat. No. 5,336,165 a dialysis machine is disclosed with which automated cleaning and disinfecting liquids can be prepared and, after termination of the dialysis treatment, stored in different lines and circuits. The solvent used for the corresponding chemicals is water, which is cleaned and sterilized before it is used. Cleaning and sterilization is effected by means of filters and membranes, a deionization device, as well as with the aid of a UV radiation source. After the end of the dialysis process, the cleaning solution is prepared by conveying the cleaned, sterilized, and prewarmed water into a chamber containing the cleaning and disinfecting chemicals which is closed during the treatment of the patient. During the procedure of dissolving the chemicals, the mixture is led into the circulation until complete dissolution is indicated with the help of conductivity probes. Cleaning of the lines as well as of the dialyzer itself is effected by reversing suitable valves following the dissolution procedure. In so doing, part of the substances contained in the cleaning solution goes over to the side of the blood circulation in accordance with the concentration gradient across the membrane of the dialyzer until a concentration balance occurs. After termination of the cleaning process, a cleaning solution of low concentration is pumped over to both the dialyzer side and the blood side until the beginning of a renewed dialysis treatment, which correspondingly inhibits microbial growth between two treatment cycles.

The drawback of such a dialysis device is that the required cleaning and/or disinfecting agents must be supplied from the outside in a condition ready for use, for example in solid or highly concentrated liquid form.

This leads to high transportation and packaging costs. Furthermore, the required disinfecting agents thus become dependent on actual availability. Moreover, the handling of such materials is possible only if there is due regard for special precautionary measures because, as a rule, aggressive, corrosive substances are involved. Also, the packaging material used for the delivery of these substances must be disposed of as waste. But the transportation problems have proven to be especially cost-intensive in practice.

The active substance most widely used worldwide for the disinfection of dialysis machines is NaOCl (bleach). However, with this highly effective disinfecting and bleaching agent, environmental pollution is especially great. On the other hand, NaOCl has the advantages of simple handling and effective cleaning/disinfection. Furthermore, in many states NaOCl is often the only disinfecting agent available.

Yet there are also other disinfecting agents in widespread use, such as, for example, peracetic acid, hydrogen peroxide, citric acid or ozone.

OBJECTS AND SUMMARY OF THE INVENTION

The object of the invention is to make available a dialysis machine that is not dependent on the delivery of the disinfecting agent.

The object of the invention is achieved by a dialysis machine having means for generating at least one disinfecting agent that can be used for disinfecting the dialysis machine. Alternatively, the invention provides a process for disinfecting a dialysis machine using a disinfecting agent wherein at least one disinfecting agent is generated on line and the disinfecting agent is brought into contact with the dialysis machine.

With the dialysis machine according to the invention, and/or the process according to the invention, it is now possible for the first time to operate dialysis devices largely independently of the availability of ready-to-use disinfecting agents, which leads to considerable savings in transportation and packaging costs. Waste disposal of the packaging materials usually required as well as long and dangerous transportation of chemicals are eliminated. In addition, far greater handling advantages accrue to the operator.

Moreover, operating safety is enhanced to the extent that dealing with aggressive, corrosive substances is largely avoided.

According to one advantageous embodiment, the dialysis machine has means for decomposing the disinfecting agent generated on line into environmentally compatible decomposition products. This ensures that after their use disinfecting agents harmful to the environment do not enter the sewage and/or the outside world.

According to one embodiment, the dialysis machine has a pipe system through which the decomposition products formed during the decomposition of at least one of the disinfecting agents, which decomposition products are reusable for the on-line generation of disinfecting agents, can be reconveyed back to the means for the on-line generation of disinfecting agents. This creates a closed recycling circuit for the production of disinfecting agents.

According to one preferred embodiment, the dialysis machine has an NaOCl generator, which produces sodium hypochlorite (NaOCl) by electrolysis of NaCl. Especially preferred for this is the use of NaCl contained in the dialysate concentrate.

In accordance with another advantageous embodiment, the dialysis machine according to the invention has a lead oxide anode for the production of ozone by electrolysis of oxygen.

According to another advantageous embodiment, a UV photo-oxidation attachment is provided by means of which UV photo-oxidation of water can be carried out. It is also possible to expose a dialysis concentrate or also a ready-to-use dialysate to UV photo-oxidation. Oxygen dissolved in water, for example, is thereby converted into ozone. Such ozone has a germicidal effect and can thus be used for the production of sterile water.

The sterile water thus produced can be added to the disinfection liquid. As a rule, it is assumed that the ozone produced by UV photo-oxidation will be used together with additional ozone.

However, the sterile water is not necessary during disinfection. Its use is to be seen, primarily, in the rerinsing operation, but also in the production of a substitute for hemofiltration and hemodialysis filtration from ultrapure water, since the latter is directly infused into the patient. Furthermore, dialysate can be produced ultrapure or, for example, supplied in advance to the blood circulation via the dialyzer.

The sterile water produced by UV photo-oxidation can also be used as rinse water, by means of which disinfecting agent residues can be removed from the dialysis machine after completion of the disinfection operation. The production of ozone in the precleaned water ensures that no recontamination of the dialysis machine by the rinse water can occur during the clean-rinsing operation.

It is possible to convert water produced by reverse osmosis (RO water) into ultrapure water. Any desired disinfecting agent can then, for example, be added to this ultrapure water, thereby ensuring optimal disinfection of the dialysis machine. As mentioned, the ultrapure water thus produced can then be used as rinse water. Furthermore, it can be used in the subsequent dialysis for the dilution of a dialysis solution concentrate with which ultrapure dialysate can be prepared.

When NaOCl is used as disinfecting agent, the dialysis machine has, according to one advantageous embodiment, a catalyst for the catalytic decomposition of NaOCl into NaCl and oxygen.

The NaCl thus formed can either be led into the waste water, thereby strongly reducing the pollution thereof, or, in accordance with another embodiment, again conveyed to the NaOCl generator.

According to another advantageous embodiment, the dialysis machine also has a device for determination of the content of disinfecting agent in the disinfection liquid used or in a rinsing liquid used thereafter.

This device for determination of the content of disinfecting agent is preferably a redox electrode. This can, for one thing, ensure that disinfecting agent is actually available and, for another, test whether disinfecting agent is still present in the dialysate circulation after the clean-rinsing operation. Such a redox electrode can easily be incorporated into a dialysis machine.

The determination of the content of disinfecting agent through the redox potential of the disinfection liquid, the rinsing liquid and/or the dialysis solution used during the actual dialysis, represents another simple and reliable procedure. The measured value indicated by the redox electrode can be advantageously used as control variable for control of the rinsing and catalysis operation.

DESCRIPTION OF THE DRAWING

FIG. 1 is a graphical representation of an embodiment of the invention.

DETAILED DESCRIPTION OF THE PREFERRED EMBODIMENT

One example of embodiment of the invention is described in greater detail below on the basis of the drawing, in which the individual components of a dialysis machine according to the invention and/or the corresponding steps of the process are schematically illustrated in a single figure.

It should be pointed out that the components illustrated can be executed by suitable means inside the dialysis machine. But it is also possible to connect a conventional dialysis machine externally to additional modules that are equipped with such means.

The use of the invention in a central preparation plant is also contemplated according to the invention.

Blood from a patient is supplied to a central dialysis unit 1 and purified and/or dialyzed in this dialysis unit 1. The blood is then conveyed back to the patient. The present invention relates to disinfection of the lines and/or sections of the dialysis unit through which the dialysate flows. As a rule, the blood side consists of disposables. To clean and disinfect the dialysate side, the dialyzer (hollow fiber filter) together with the disposables are removed and discarded, and the connections to the dialyzer are short-circuited. In case of reuse of the dialyzer, it can also remain in the circulation and be codisinfected, but this requires a membrane-compatible disinfecting agent. Separation from the blood side occurs via the semipermeable membrane of the dialyzer.

RO water is supplied to a UV photo-oxidation chamber 2. There, the water is exposed to UV radiation, for example, the UV radiation of a low-pressure mercury lamp. UV light in the spectral range of 200 to 300 nanometers kills microorganisms by destroying the DNA of the cells. Low-pressure mercury lamps produce the greatest energy at a wave length of 254 nanometers. This level is very close to the optimal wave length for sterilization, which is 260 nanometers.

Specially developed lamps, in which only high-purity quartz is used, further permit radiation of a wave length at 185 nm. The combined action that occurs from the UV light at the wavelengths of 185 nm and 254 nm effects the photo-oxidation of dissolved organic compounds.

The emission of UV light at 185 nm catalyzes the reaction of oxygen dissolved in water to ozone. Upon dissociation, the ozone thus produced kills the germs present in the water.

Altogether, ultrapure water can be produced by UV photo-oxidation of the RO water. If necessary, additional ozone can be added to this ultrapure water for disinfection, as is schematically shown in the drawing. As a rule, however, the ultrapure water is used for rinsing, in order to again remove disinfecting agents. Furthermore, it is used for dilution of the dialysis concentrate.

The added ozone can be produced by means of the electrolysis of water with lead dioxide anodes 8 or by means of a Siemens process. The use of this electrolytic oxidation process with lead dioxide anodes offers advantages compared to other generation processes in that there is no formation of gas and that high concentrations can be achieved. There are, of course, also other conceivable processes for the production of ozone. Moreover, the supply of ready-made ozone is likewise possible.

The electrolytic production of NaOCl occurs in a generator 3. In the preferred production process, approximately 10% sodium chloride solution is electrolyzed in such a way that the chlorine set free at the positive pole and the NaOH formed at the negative pole react with each other according to the equation $Cl_2+2NaOH=NaOCl+NaCl+H_2O$.

The NaOCl thus formed is conveyed to the (ultrapure) water in the desired ratio, but does not need any ultrapure water to carry out the disinfection effect.

The disinfecting agent thus produced is conveyed to the central dialysis unit 1 via the feed mechanism 7.

Ozone has advantages in that it is less detrimental to a dialysis membrane if the dialyzer remains in the machine or if the dialysis machine has a so-called Diasafe, or on-line, filter.

Moreover, ozone has the advantage with regard to wastewater pollution in that it is relatively unstable and decomposes after a while.

It is likewise conceivable for special applications to ensure the disinfection of a medical device solely with ozone.

Ozone can also be advantageously used for the germ-free conservation of water over several days. In particular, a home dialysis machine is used only every two to three days. A sufficient ozone content of the water remaining in the device prevents microbial growth until the next use.

The dialysis machine is disinfected with the ozone produced or with the NaOCl produced. But before the actual dialysis procedure, the machine must be rerinsed with a rinsing liquid in order to remove residues of the disinfecting agent. In order not to recontaminate the machine with germs in the rinse water, the latter uses both RO water as well as water rendered sterile according to the invention by means of photo-oxidation. The combination is deemed to be especially preferable. This sterile water can also be used for the dialysis that follows in order to dilute the concentrate of a dialysis solution as desired.

To monitor flawless disinfection and/or rerinsing, a redox electrode 5 is provided, by means of which the redox potential of disinfection liquids can be determined. Determination of the redox potential makes possible the determination of the content of disinfecting agent in the disinfecting liquid. The redox electrode serves to verify the presence of a sufficient amount of disinfecting agent during the disinfection process in order to thus ensure the proper course of the disinfection program. It further serves to verify that the dialysis machine has been properly rinsed clean before it is connected to the patient for the next dialysis.

The redox electrode serves primarily for the detection of disinfecting agent in determining whether the dialysis machine has been completely rinsed clean.

In addition to the determination of the presence of disinfecting agent, the measured values determined by the redox electrode can be used as control variables for control of the disinfection, rinsing, and catalysis operations.

Such a redox electrode can be built into a dialysis machine. Verification that the machine has been rinsed clean, which at the present time still needs to be carried out manually, for example by means of test strips (potassium iodide starch paper, peroxide test, etc.), can be dispensed with.

The provision of a redox electrode makes the simple control of the disinfection program possible and offers an additional protective function during the dialysis.

Finally, the used disinfection liquid is conveyed to a catalyst device 6, which effects the catalytic decomposition of the NaOCl into the components NaCl and $O_2$.

This catalyst device 6 can also be easily incorporated into the dialysis machine. Furthermore, it can be provided externally or centrally for a plurality of machines at a dialysis station.

The NaCl produced during the catalytic reaction can then be conveyed to the NaOCl generator 3 through a pipe system 9. Thus, a closed circuit for the production and catalytic decomposition of NaOCl is created. The starting substances NaCl and $H_2O$ react to form NaOCl, which dissociates into NaCl and $O_2$ after its catalytic decomposition.

These starting products do not cause any hazards. The risk of corrosive injury to the operator of the machine as well as environmental hazards can be excluded.

The various devices can be arranged inside a dialysis machine. An integrated dialysis machine is thus made available which offers important operating simplification over conventional devices.

As mentioned, the process according to the invention can be incorporated in such a dialysis machine. It is, however, likewise possible to carry out at least one of the steps of the process, such as UV photo-oxidation, generation of NaOCl, production of ozone, determination of the content of disinfecting agent by means of a redox electrode, or the catalytic decomposition of NaOCl, externally, i.e., through a central supply unit.

What is claimed is:

1. A system for disinfecting a medical apparatus comprising:
   (a) an integrated means for chemical generation of at least one disinfecting agent;
   (b) a feed mechanism in fluid communication with the chemical generation means;
   (c) a medical apparatus in fluid communication with the feed mechanism; and
   (d) a catalytic decomposition unit connected to the medical apparatus, which is adapted to receive or decompose the disinfecting agent.

2. The system according to claim 1 wherein the medical apparatus is a dialysis machine.

3. The system according to claim 1 wherein the disinfecting agent is selected from the group consisting of NaOCl, ozone, and mixtures thereof.

4. A system for the disinfection of a dialysis machine, comprising:
   a. a NaOCl generator in fluid communication with a feed mechanism;
   b. an ozone generator in fluid communication with the feed mechanism;
   c. a means for combining NaOCl, or ozone, or mixtures thereof with ultrapure water, to produce a disinfecting solution for disinfecting the dialysis machine;
   d. means for feeding the disinfecting solution through the dialysis machine, which is connected to the combining means;
   e. a decomposition unit having an inlet in fluid communication with the dialysis machine, wherein the unit is constructed and arranged for decomposing the NaOCl and ozone in the disinfecting solution flowing from the dialysis machine into NaCl and $O_2$, following the disinfection of the dialysis machine; and f. means in communication with an outlet of the decomposition unit for providing some portion of the NaCl formed by decomposition to the NaOCl generator.

5. The system of claim 4 wherein the system is located external to the dialysis machine.

6. The system of claim 4 wherein the system is integrated into the dialysis machine.

7. A medical apparatus, comprising: a dialysis machine including a system for disinfecting the dialysis machine comprising:

a. NaOCl generator in fluid communication with a feed mechanism;

b. an ozone generator in fluid communication with the feed mechanism;

c. a means for combining NaOCl, ozone, or mixtures thereof with ultrapure water to produce a disinfecting solution for disinfecting the dialysis machine;

d. means for feeding the disinfecting solution through a dialysate flow path in the dialysis machine, wherein the feeding means is connected to the combining means;

e. means for rinsing the dialysis machine with ultrapure water following disinfection;

f. a redox electrode connected to the dialysate flow path, which is constructed and arranged for determining the amount of disinfectant in the dialysis machine;

g. a catalytic decomposition unit connected to the dialysate flow path, which is constructed and arranged for receiving the disinfecting solution and for decomposing the NaOCl and ozone in the disinfecting solution into NaCl and $O_2$ following disinfection; and h. providing means connected to the catalytic decomposition unit for providing some or all of the NaCl formed in the decomposition unit to the NaOCl generator.

8. The apparatus according to claim 7 further comprising means for controlling the disinfection, catalytic decomposition and rinsing of the dialysis machine based on disinfectant levels determined by the redox electrode.

9. The apparatus according to claim 7 wherein the dialysis machine further comprises a UV photo-oxidation unit connected to the rinsing means for the production of rinse water selected from the group consisting of ultrapure water, sterile water and mixtures thereof, and wherein the dialysis machine is rinsed with the rinse water.

10. A process for disinfecting a medical apparatus which comprises chemically generating at least one disinfecting agent on-line, contacting the areas of the medical apparatus to be disinfected with the disinfecting agent, and decomposing the disinfecting agent.

11. The process according to claim 10 wherein the medical apparatus is a dialysis machine.

12. The process according to claim 10 wherein the disinfecting agent is selected from the group consisting of NaOCl, ozone and mixtures thereof.

13. The process according to claim 12 wherein the NaOCl is decomposed into NaCl and $O_2$ or other environmentally compatible decomposition products.

14. The process of claim 10 further comprising combining the disinfectant produced on-line with ultrapure water to form a disinfecting solution and contacting the medical apparatus with the disinfecting solution.

15. The process of claim 14 wherein the ultrapure water is formed by subjecting reverse osmosis water to UV photo-oxidation.

16. The process of claim 15 wherein the UV photo-oxidation is provided by either a low pressure mercury lamp, a high purity quartz lamp, or a combination thereof.

17. The process according to claim 10 further comprising rinsing the medical apparatus using ultrapure water, sterile water, or mixtures thereof.

18. A process for disinfecting a dialysis machine, which comprises:

a. producing NaOCl using an on-line NaOCl generator;

b. combining the NaOCl with ultrapure water to produce a disinfecting solution;

c. contacting the areas of the dialysis machine to be disinfected with the disinfecting solution;

d. catalytically decomposing the NaOCl into NaCl and $O_2$ after the dialysis machine has been disinfected;

e. providing NaCl to the NaOCl generator for on-line production of NaOCl;

f. determining the amount of disinfectant present in the dialysis machine using a redox electrode; and g. rinsing the dialysis machine to remove disinfectant after disinfection.

19. The process according to claim 18 further comprising producing ozone using an on-line ozone generator and combining the ozone with the ultrapure water to form a disinfecting solution.

20. The process according to claim 18 further comprising controlling the disinfection, rinsing or catalytic decomposition processes according to the level of disinfectant determined by the redox electrode.

21. The process according to claim 18 wherein the dialysis machine is rinsed using ultrapure water, sterile water or mixtures thereof.

22. The process according to claim 18 wherein the process is carried out within the dialysis machine.

23. The process according to claim 18 wherein one or more steps are carried out external to the dialysis machine.

24. A system for disinfecting a medical apparatus comprising:

(a) an integrated means for chemical generation of at least one disinfecting agent;

(b) a feed mechanism in fluid communication with the chemical generation means;

(c) a medical apparatus in fluid communication with the feed mechanism; and (d) means for decomposing the disinfecting agent that is in fluid connection with the medical apparatus and is constructed and arranged for accepting and decomposing the disinfecting agent after it contacts the medical apparatus, wherein the disinfecting agent generation means provides the disinfecting agent to the medical apparatus via the feed mechanism, the disinfecting agent flows through the medical apparatus and into the decomposition means where it is decomposed.

25. The system according to claim 24 wherein the disinfecting agent is capable of being decomposed into NaCl and $O_2$ or other environmentally compatible decomposition products.

26. The system according to claim 25 further comprising a pipe system, or other conduction system, for providing some portion of the NaCl produced through decomposition of NaOCl to the NaOCl generator.

27. A process for disinfecting a medical apparatus which comprises chemically producing at least one disinfecting agent on-line, contacting the areas of the medical apparatus to be disinfected with the disinfecting agent, and decomposing the disinfecting agent after the medical apparatus has been contacted.

28. A system for disinfecting a medical apparatus comprising:
   (a) an integrated means for chemical generation of at least one disinfecting agent;
   (b) a feed mechanism in fluid communication with the chemical generation means;
   (c) a medical apparatus in fluid communication with the feed mechanism;
   and
   (d) a redox electrode connected to the medical apparatus for determining the level of disinfecting agent remaining in the medical apparatus.

29. A process for disinfecting a medical apparatus which comprises chemically generating a disinfecting agent selected from the group consisting of NaOCl, ozone and mixtures thereof, contacting the areas of the medical apparatus to be disinfected with the disinfectant, and decomposing the NaOCl into NaCl and $O_2$ or other environmentally compatible decomposition products.

30. A process disinfecting a medical apparatus which comprises chemically producing at least one disinfecting agent on-line, contacting the areas of the medical apparatus to be disinfected with the disinfectant, and determining the amount of disinfectant present in the apparatus using a redox electrode.

* * * * *